(12) United States Patent
Lee et al.

(10) Patent No.: US 12,207,657 B2
(45) Date of Patent: Jan. 28, 2025

(54) METHODS OF MULTI-SPECIES INSECT PEST CONTROL

(71) Applicant: Fraunhofer-Gesellschaft zur Foerderung der angewandten Forschung e.V., Munich (DE)

(72) Inventors: Kwang-Zin Lee, Hannover (DE); Andreas Vilcinskas, Fernwald (DE)

(73) Assignee: Fraunhofer-Gesellschaft zur Foerderung der angewandten Forschung e.V., Munich (DE)

(*) Notice: Subject to any disclaimer, the term of this patent is extended or adjusted under 35 U.S.C. 154(b) by 609 days.

(21) Appl. No.: 17/192,764

(22) Filed: Mar. 4, 2021

(65) Prior Publication Data

US 2021/0274790 A1 Sep. 9, 2021

(30) Foreign Application Priority Data

Mar. 5, 2020 (EP) .................................. 20161166

(51) Int. Cl.
*A01N 63/32* (2020.01)
*C12N 1/14* (2006.01)
*C12N 1/16* (2006.01)
*C12R 1/84* (2006.01)

(52) U.S. Cl.
CPC ............. *A01N 63/32* (2020.01); *C12N 1/145* (2021.05); *C12R 2001/84* (2021.05)

(58) Field of Classification Search
CPC ........ A01N 63/32; A01N 25/04; C12N 1/145; C12N 1/165; C12N 1/16; C12R 2001/84
See application file for complete search history.

(56) References Cited

U.S. PATENT DOCUMENTS

| | | | |
|---|---|---|---|
| 2013/0045301 A1 | 2/2013 | Swiegers et al. | |
| 2017/0226451 A1 | 8/2017 | Saerens et al. | |
| 2019/0387748 A1* | 12/2019 | Martinez | A01N 63/50 |

FOREIGN PATENT DOCUMENTS

| | | | |
|---|---|---|---|
| CN | 108676732 | * | 10/2018 |
| CN | 108676732 A | * | 10/2018 |

OTHER PUBLICATIONS

EP20161166.2 Extended European Search Report mailed Aug. 4, 2020.

Vacek et al. "Relevance of the Ecology of Citrus Yeasts to the Diet of *Drosophila*," Microbial Ecology, 1979, 5:43-49.
Pintar et al. "The costs and benefits of killer toxin production by the yeast *Pichia kluyveri*," Antonie van Leeuwenhoek, 2003, 83:89-97.
Piper et al. "Two Gut-Associated Yeasts in a Tephritid Fruit Fly have Contrasting Effects on Adult Attraction and Larval Survival," J Chem Ecol, 2017, 43:891-901.
Scheidler et al. "Volatile codes: Correlation of olfactory signals and reception in *Drosophila*-yeast chemical communication," Scientific Reports, Sep. 22, 2015, 5:14059, 1-13.
Lewis et al. "Differential Impacts of Yeasts on Feeding Behavior and Development in Larval *Drosophila suzukii* (Diptera:Drosophilidae)," Scientific Reports, Sep. 16, 2019, 9:13370, 1-12.
Mewa-Ngongang et al. "Fungistatic and fungicidal properties of *Candida pyralidae* Y1117, *Pichia kluyveri* Y1125 and *Pichia kluyveri* Y1164 on the biocontrol of *Botrytis cinerea*," 10th Int'l Conference on Advances in Science, Engineering, Technology & Healthcare, Nov. 2018, 29-32.
Beckmann et al. "Insektizide für die Landwirtschaft: Chemische Schädlingsbekämpfung (Chemical pest control: Insecticides for agriculture)," Chem. Our Time, 2003, 37:88-97.
Hallmann et al. "More than 75 percent decline over 27 years in total flying insect biomass in protected areas," PLoS One, Oct. 18, 2017, 12(10):e0185809 (1-21).
Tsvetkov et al. "Chronic exposure to neonicotinoids reduces honey bee health near corn crops," Science, Jun. 30, 2017, 356:1395-1397.
Whitehorn et al. "Neonicotinoid Pesticide Reduces Bumble Bee Colony Growth and Queen Production," Science, Apr. 20, 2012, 336:351-352.
Rundlöf et al. "Seed coating with a neonicotinoid insecticide negatively affects wild bees," Nature, May 7, 2015, 521:77-80.
Cassereau et al. "Neurotoxicity of Insecticides," Current Medical Chemistry, 2017, 24:2988-3001.
Phaff et al. "*Pichia barkeri*, a New Yeast Species Occurring in Necrotic Tissue of *Opuntia stricta*," International Journal of Systematic Bacteriology, Oct. 1987, 37(4):386-390.
Masoud et al. "Pectin degrading enzymes in yeasts involved in fermentation of *Coffea arabica* in East Africa," International Journal of Food Microbiology, 2006, 110:291-296.
Björnberg et al. "Inhibition of the growth of grain-storage molds in vitro by the yeast *Pichia anomala* (Hansen) Kurtzman," Can. J. Microbiol., 1993, 39:623-628.

* cited by examiner

*Primary Examiner* — Mina Haghighatian
(74) *Attorney, Agent, or Firm* — Wagenknecht IP Law Group PC

(57) ABSTRACT

Multi-species pest control methods, which contact or subject a target pest to a yeast strain belonging to the species *Pichia kluyveri* and/or with a lysate, filtrate, isolate or extract thereof. The yeast strain belonging to the species *Pichia kluyveri* and/or the lysate, filtrate, isolate or extract thereof is incorporated into the body of the agricultural target pest.

8 Claims, 7 Drawing Sheets

Specification includes a Sequence Listing.

Fungal ITS forward primer: (SEQ ID NO. 1)

GGAAGTAAAAGTCGTAACAAGG

Fungal ITS reverse primer: (SEQ ID NO. 2)

GCTGCGTTCTTCATCGATGC

FIG. 5

60EH52 (SEQ ID NO. 3)

GATCTGAGGTCGAGCTTAGTTAAAAGTTCGGCGGCCAAAGCGTGCTAAAAGTTTAGTTC
ACTTCGTCCACGACGTTCCATTTCGAAAAAGGCATAGCCTGTTCTCAACTCTGCTTGCGC
AAGAAGGAAACGACGCTCAGACAGGCATGCCCCATGGAATACCATGGGGCGCAATGTG
CGTTCAAGAACTCGATGATTCACGATGGCTGCAATTCACACTAGGTATCGCATTTCGCT
GCGTTCTTCATCGATGCAAATGCGACAAAATCC

60EH51 (SEQ ID NO. 4)

TCGAGTTCTTGAACGCACATTGCGCCCCATGGTATTCCATGGGGCATGCCTGTCTGAGC
GTCGTTTCCTTCTTGCGCAAGCAGAGTTGAGAACAGGCTATGCCTTTTTCGAAATGGAA
CGTCGTGGACGAAGTGAACTAAACTTTTAGCACGCTTTGGCCGCCGAACTTTTAACTAA
GCTCGACCTCAGATCAGGTAGGAATACCCGCTGAACTTAAGCATATCAATAAGCGGAG
GAA

60EH49 (SEQ ID NO. 5)

GATCATTACTGTGATTTATATCTTATACACATGCGTGAGCGCACCAAACACCTAAAATT
GTAATAATACCAGTCACTAAGTTTTAACAAAACAAAACTTTCAACAACGGATCTCTTGG
TTCTCGCATCGATGAAGAACGC

FIG. 6

60EH48 (SEQ ID NO. 6)

AGACTTTGATTTCTCGTAAGGTGCCGAGTGGGCAAGAAGCGCCACCCGATCCCTAGTCG
GCATAGTTTATGGTTAAGACTACGACGGTATCTGATCATCTTCGATCCCCTAACTTTCGT
TCTTGATTAATGAAAACGTCCTTGGCAAATGCTTTCGCAGTAGTTAGTCTTCAGTTAATC
CAAGAATTTCACCTCTGACAACTGAATACTGATGCCCCGACCGTCCCTATTAATCATT
ACGATGGTCCTAGAAACCAACAAATAGAACCATAACGTCCTATTCTATTATTCCATGC
TAATATATCCGAGCAAAGGCCTGCTTTGAACACTCTAATTTCCTCAAAGTAATCGTCCT
GGTTCACTCCAAAAAGTTAGCCAGAAGGAAAAGACCCGGCCGCAACAGTACTTACCAT
AGGTAGACCGCCCGCCCAGGCCCAAAGTTCAACTACGAGCTTTTAACTGCAACAACTT
TAATATACGCTATTGGAGCTGGAATTACCGCGGCG

60EH47 (SEQ ID NO. 7)

GCTCGTAGTTGAACTTTGGGCCTGGGCGGGCGGTCTACCTATGGTAAGTACTGTTGCGG
CCGGGTCTTTTCCTTCTGGCTAACTCTTCGGAGTGAACCAGGACGATTACTTTGAGGAA
ATTAGAGTGTTCAAAGCAGGCCTTTGCTCGGATATATTAGCATGGAATAATAGAATAG
GACGTTATGGTTCTATTTTGTTGGTTTCTAGGACCATCGTAATGATTAATAGGGACGGT
CGGGGGCATCAGTATTCAGTTGTCAGAGGTGAAATTCTTGGATTAACTGAAGACTAACT
ACTGCGAAAGCATTTGCCAAGGACGTTTTCATTAATCAAGAACGAAAGTTAGGGGATC
GAAGATGATCAGATACCGTCGTAGTCTTAACCATAAACTATGCCGACTAGGGATCGGG
TGGCGCTTCTTGCCCACTCGGCACCTTACGAGAAATCAAAGTCTTTGGGTTCTGGGGGG
AGTATGGTTGCAAGGCTGAAACTCAAAGGAATTGACGG

FIG. 7

SEQUENCE LISTING

<160> NUMBER OF SEQ ID NOS: 7

<210> SEQ ID NO 1
<211> LENGTH: 22
<212> TYPE: DNA
<213> ORGANISM: Artificial Sequence
<220> FEATURE:
<223> OTHER INFORMATION: Fungal ITS forward primer

<400> SEQUENCE: 1
ggaagtaaaa gtcgtaacaa gg                                              22

<210> SEQ ID NO 2
<211> LENGTH: 20
<212> TYPE: DNA
<213> ORGANISM: Artificial Sequence
<220> FEATURE:
<223> OTHER INFORMATION: Fungal ITS reverse primer

<400> SEQUENCE: 2
gctgcgttct tcatcgatgc                                                 20

<210> SEQ ID NO 3
<211> LENGTH: 269
<212> TYPE: DNA
<213> ORGANISM: Pichia kluyveri

<400> SEQUENCE: 3
gatctgaggt cgagcttagt taaaagttcg gcggccaaag cgtgctaaaa gtttagttca     60
cttcgtccac gacgttccat ttcgaaaaag gcatagcctg ttctcaactc tgcttgcgca    120
agaaggaaac gacgctcaga caggcatgcc ccatggaata ccatggggcg caatgtgcgt    180
tcaagaactc gatgattcac gatggctgca attcacacta ggtatcgcat ttcgctgcgt    240
tcttcatcga tgcaaatgcg acaaaatcc                                      269

<210> SEQ ID NO 4
<211> LENGTH: 238
<212> TYPE: DNA
<213> ORGANISM: Pichia kluyveri

<400> SEQUENCE: 4
tcgagttctt gaacgcacat tgcgccccat ggtattccat ggggcatgcc tgtctgagcg     60
tcgtttcctt cttgcgcaag cagagttgag aacaggctat gccttttttcg aaatggaacg   120 tcgtggacga agtgaactaa acttttagca cgctttggcc gccgaacttt taactaagct    180
cgacctcaga tcaggtagga atacccgctg aacttaagca tatcaataag cggaggaa     238

<210> SEQ ID NO 5
<211> LENGTH: 140
<212> TYPE: DNA
<213> ORGANISM: Pichia kluyveri

<400> SEQUENCE: 5
gatcattact gtgatttata tcttatacac atgcgtgagc gcaccaaaca cctaaaattg     60
taataatacc agtcactaag ttttaacaaa acaaaacttt caacaacgga tctcttggtt   120
ctcgcatcga tgaagaacgc                                                140

<210> SEQ ID NO 6
<211> LENGTH: 508
<212> TYPE: DNA
<213> ORGANISM: Pichia kluyveri

```
<400> SEQUENCE: 6
agactttgat ttctcgtaag gtgccgagtg ggcaagaagc gccacccgat ccctagtcgg    60
catagtttat ggttaagact acgacggtat ctgatcatct tcgatcccct aactttcgtt   120
cttgattaat gaaaacgtcc ttggcaaatg ctttcgcagt agttagtctt cagttaatcc   180
aagaatttca cctctgacaa ctgaatactg atgcccccga ccgtccctat taatcattac   240
gatggtccta gaaaccaaca aaatagaacc ataacgtcct attctattat tccatgctaa   300
tatatccgag caaaggcctg ctttgaacac tctaatttcc tcaaagtaat cgtcctggtt   360
cactccaaaa agttagccag aaggaaaaga cccggccgca acagtactta ccataggtag   420
accgcccgcc caggcccaaa gttcaactac gagcttttta actgcaacaa ctttaatata   480
cgctattgga gctggaatta ccgcggcg                                      508

<210> SEQ ID NO 7
<211> LENGTH: 507
<212> TYPE: DNA
<213> ORGANISM: Pichia kluyveri

<400> SEQUENCE: 7
gctcgtagtt gaactttggg cctgggcggg cggtctacct atggtaagta ctgttgcggc    60
cgggtctttt ccttctggct aactcttcgg agtgaaccag gacgattact ttgaggaaat   120
tagagtgttc aaagcaggcc tttgctcgga tatattagca tggaataata gaataggacg   180
ttatggttct attttgttgg tttctaggac catcgtaatg attaataggg acggtcgggg   240
gcatcagtat tcagttgtca gaggtgaaat tcttggatta actgaagact aactactgcg   300
aaagcatttg ccaaggacgt tttcattaat caagaacgaa agttagggga tcgaagatga   360
tcagataccg tcgtagtctt aaccataaac tatgccgact agggatcggg tggcgcttct   420
tgcccactcg gcaccttacg agaaatcaaa gtctttgggt tctgggggga gtatggttgc   480
aaggctgaaa ctcaaaggaa ttgacgg                                       507
```

METHODS OF MULTI-SPECIES INSECT PEST CONTROL

CROSS REFERENCE TO RELATED APPLICATIONS

This application claims benefit of priority to European patent application no. 20161166.2, filed Mar. 5, 2020, the entire content of which is herein incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with the file "EP20161166-2-SEQUENCES" created on 4 Mar. 2021 and having a size of 4 Kilobytes. The sequence listing contained in this ASCII formatted document forms part of the specification and is herein incorporated by reference in its entirety.

TECHNICAL FIELD

The invention relates to multi-species pest control methods, which contact/subject a target pest with a yeast strain belonging to the species *Pichia kluyveri* and/or with a lysate, filtrate, isolate or extract thereof. In particular, the yeast strain belonging to the species *Pichia kluyveri* and/or a lysate, filtrate, isolate or extract thereof is incorporated into the body of an agricultural target pest.

BACKGROUND

The environment in which humans live is replete with pest infestation. Pests including insects, arachnids, crustaceans, fungi, bacteria, viruses, nematodes, flatworms, roundworms, pinworms, hookworms, tapeworms, trypanosomes, schistosomes, botflies, fleas, ticks, mites, and lice and the like are pervasive in the human environment. For example, insects of the order Hemiptera including aphids are significant pests of crops and garden plants as well as ornamentals.

Insects of the family Drosophilidae are a diverse, cosmopolitan family of flies, which includes fruit flies. For example, *Drosophila suzukii*, commonly called the spotted wing *drosophila* or SWD, is a fruit fly. *D. suzukii*, originally from Southeast Asia, is becoming a major pest species in the United States of America and Europe, because it infests fruit early during the ripening stage, in contrast with other *Drosophila* species that infest only rotting fruit. This species is classified as a pest due to its rapid reproduction and ability to cause damage to ripening soft fruits such as cherries, blueberries and strawberries. Females are capable of cutting through the skin of soft fruit using a sharp ovipositor and subsequently lay eggs inside. This can cause crop losses up to 80%, leading to potential economical disasters.

Even though *Drosophila suzukii* has been reported throughout America and Western Europe since 2008, no clear species-specific integrated pest management (IPM) strategy has been described Many potential IPM strategies such as attract-and-kill, mass trapping and mating disruption involve the usage of pheromones. However, relatively little is known about pheromones in *D. suzukii* and results obtained in the well-studied model organism *Drosophila melanogaster* are often different or even opposite to results obtained in *D. suzukii*.

As a further example, aphids are the most common vectors of plant viruses, transmitting nearly 30% of all known virus species. They typically vector so-called non-persistent viruses, such as the highly diverse viruses of the family Potyviridae (Brault et al, 2010). Non-persistent virus infections occur a few minutes after mechanical inoculation via the aphid stylet, which is a mouthpart specialized for the penetration of plant tissue. These viruses are also of great economic importance. All of the devastating aphid species listed above act as vectors for plant viruses (Brault et al., 2010). In addition to the damage caused by direct feeding, virus-infected plants may show a range of symptoms including leaf yellowing and curling, growth abnormalities, and ultimately death.

Annual worldwide crop losses due to aphids and the viral diseases they carry have been valued at hundreds of millions of euros (The International Aphid Genomics, 2010). In Australia alone, the losses caused by aphid feeding and disease transmission amount to €210 million and €420 million per year, respectively. The global cost associated with the management of sharka disease, which is caused by aphid-transmitted Plum pox virus (Potyviridae), exceeded €10 billion between 1976 and 2006. This disease affects many stone fruits and is one of the most widely studied viral diseases.

Intensive plant trade and global warming provide opportunities for the introduction of new aphid species and their associated viruses to formerly unaffected regions. More than 100 aphid species originating from other continents are now well established in Europe. Invasive species of insects and pathogens pose a serious threat to crops. In the United States, crop and forest production losses from aphids can exceed €30 billion per year.

Chemical insecticides have long been used to control pest insects, including aphids. In the 1940s, new synthetic organic insecticides such as dichlorodiphenyltrichloroethane (DDT) and organophosphates led to great improvements in insecticidal efficacy and were subsequently used globally for pest control. Not surprisingly, this resulted in the rapid selection of resistant insect populations and species. As more insecticidal compounds are discovered, the same selection process occurs, encapsulating the concept of an evolutionary arms race between humans and pest insects (Sparks and Nauen, 2015). Despite the widespread use of insecticides, 18-20% of global crops are still lost to damage and disease caused by insect pests.

Because most plants are infested by more than one pest species, an approach is needed whose efficiency does not differ between different species.

Therefore, the availability of improved pest control methods for numerousness pest species would be highly advantageous.

SUMMARY OF THE DISCLOSURE

The present disclosure pertains to multi-species pest control methods comprising contacting/subjecting a target pest with a yeast strain belonging to the species *Pichia kluyveri* and/or with a lysate, filtrate, isolate or extract thereof. In particular, the yeast strain belonging to the species *Pichia kluyveri* and/or a lysate, filtrate, isolate or extract thereof is incorporated into the body of an agricultural target pest e.g. by feeding of the target pest.

The present disclosure pertains in particular to an isolated strain of the species *Pichia kluyveri* having a deposit accession number DSMZ 33403 and yeast strains derived therefrom, progenies or mutants thereof, wherein the mutants thereof retaining the properties of said isolated strain, wherein in particular a property is to reduce the survival of a target pest.

Furthermore, the present disclosure pertains to lysates, filtrates, isolates or extracts of the isolated strains according to the present disclosure, in particular of the isolated strain of the species *Pichia kluyveri* and in particular of a strain having a deposit accession number DSMZ 33403 and yeast strains derived therefrom, progenies or mutants thereof, wherein the mutants thereof retaining the properties of said isolated strain, wherein in particular a property is to reduce the survival of a target pest.

In a further aspect, embodiments of the disclosure provide the novel pest control methods comprising incorporating a yeast strain belonging to the species *Pichia kluyveri* and/or a lysate, filtrate, isolate or extract thereof into the body of an agricultural target pest, wherein the target pest is an insect belonging to the order Hemiptera, in particular wherein the target pest belonging to the suborder Sternorrhyncha and/or to the infraorder Fulgoromorpha, in particular wherein the target pest belonging to the family of aphids like *Acyrthosiphon pisum* and/or wherein the target pest is an insect belonging to the family Drosophilidae, in particular wherein the target pest belonging to the genus *Drosophila*, in particular wherein the target pest belonging to the species of *Drosophila suzukii* and/or *Drosophila melanogaster*, and the uptake by the target pest of said yeast strain and/or a lysate, filtrate, isolate or extract thereof reduces at least the survival rate of said target pest.

In a further aspect, embodiments of the disclosure provide the novel use of a yeast strain belonging to the species *Pichia kluyveri* and/or a lysate, filtrate, isolate or extract thereof as a pest control agent against a target pest, in particular wherein the strain is *Pichia kluyveri* EPY-1 (DSMZ Accession number 33403) and the survival of the target pest is reduced. In particular, the yeast strain belonging to the species *Pichia kluyveri* can be identified with the ITS primers SEQ ID NO: 1 and SEQ ID NO:2, or homologs thereof, wherein said homologs may have a sequence identity of at least 80%, in particular of at least 85%, in particular of at least 90%, in particular of at least 95, 96%, 97%, 98%, 99% to SEQ ID NO: 1 and/or SEQ ID NO:2. In an advantageous example, the used yeast strain belonging to the species *Pichia kluyveri* comprises an ITS sequence selected from the group consisting of SEQ ID NO:3, SEQ ID NO:4, SEQ ID NO:5, SEQ ID NO:6 and SEQ ID NO:7 or homologs thereof, wherein said homologs may have a sequence identity of at least 80%, in particular of at least 85%, in particular of at least 90%, in particular of at least 95, 96%, 97%, 98%, 99% to SEQ ID NO:3, SEQ ID NO:4, SEQ ID NO:5, SEQ ID NO:6 or SEQ ID NO:7.

In a further aspect, embodiments of this disclosure relate to compositions comprising a carrier and a yeast strain belonging to the species *Pichia kluyveri* and/or a lysate, filtrate, isolate or extract thereof as a pest control agent against a target pest, in particular wherein the strain is *Pichia kluyveri* EPY-1 (DSMZ Accession number 33403) and the survival of the target pest is reduced.

In a further aspect, some embodiments provide methods for controlling Hemiptera and/or *Drosophila* pest infestation comprising providing in the diet of a Hemiptera and/or *Drosophila* pest an agent comprising a yeast strain belonging to the species *Pichia kluyveri* and/or a lysate, filtrate, isolate or extract thereof as a pest control agent against a target pest, in particular wherein the strain is *Pichia kluyveri* EPY-1 (DSMZ Accession number 33403) and the survival of the target pest is reduced.

Before the disclosure is described in detail, it is to be understood that this disclosure is not limited to the particular component parts of the process steps of the methods described. It is also to be understood that the terminology used herein is for purposes of describing particular embodiments only and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

BRIEF DESCRIPTION OF THE DRAWINGS

FIG. 5 shows the nucleic acid sequences of the ITS primers used for amplification (SEQ ID NO. 1 and SEQ ID NO. 2).

FIGS. 6-7 show the ITS nucleic acid sequences of the identified *Pichia kluyveri* EPY-1 strain (SEQ ID NO. 3 to 7).

DETAILED DESCRIPTION OF THE DISCLOSURE

Figure 1:
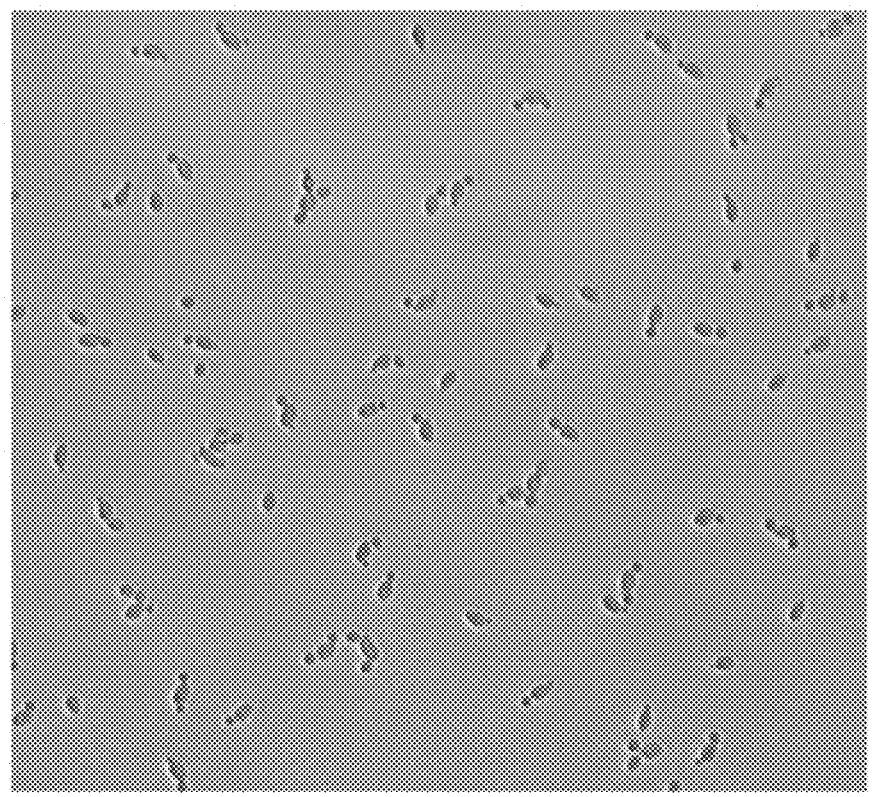
FIG. 1 shows a microscopic analysis of the yeast strain *Pichia kluyveri* EPY-1 displaying the elliptic shape of the cells.

The present disclosure pertains to the use of *P. kluyveri* and/or of a lysate, filtrate, isolate or extract thereof as a biological insecticide (Biological). Based on the present disclosure it is the first time that insectpathogenic properties are attributed to *P. kluyveri* strains, in particular against insects belonging to the family Drosophilidae, in particular wherein the target pest belonging to the genus *Drosophila*, in particular wherein the target pest belonging to the species of *Drosophila suzukii* and/or *Drosophila melanogaster*.

Therefore, disclosed herein are novel pest control methods comprising the incorporation of a yeast strain belonging to the species *Pichia kluyveri* and/or of a lysate, filtrate, isolate or extract thereof into a target pest. In particular, the yeast strain belonging to the species *Pichia kluyveri* and/or a lysate, filtrate, isolate or extract thereof is incorporated into the body of an agricultural target pest by feeding.

Therefore, the present disclosure relates to methods of inhibiting the survival of a target pest, whereby the method comprises contacting said target pest with a yeast strain belonging to the species *Pichia kluyveri* and/or with a lysate, filtrate, isolate or extract thereof.

Surprisingly, the inventors found that contacting insects with yeast strains belonging to the species *Pichia kluyveri* is a universally applicable form of a multi-species target pest control in particular for a control of target pests belonging to the order Hemiptera, in particular belonging to the suborder Sternorrhyncha, and in particular belonging to the family of aphids like *Acyrthosiphon pisum* and insects belonging to the family Drosophilidae, in particular wherein the target pest belonging to the genus *Drosophila*, in particular wherein the target pest belonging to the species of *Drosophila suzukii* and/or *Drosophila melanogaster*.

In an advantageous embodiment of the present disclosure, the inventors identify the novel *Pichia kluyveri* EPY-1 strain that was deposited on Jan. 17, 2020 under the accession number DSM 33403 according to the requirements of the Budapest Treaty at the Deutsche Sammlung von Mikroorganismen und Zellkulturen (DSMZ), Inhoffenstraße 7B, 38124 Braunschweig (DE) by Fraunhofer Institute for Molecular Biology and Applied Economy IME, Winchester-str.2, 35394 Giessen, Germany. All restrictions on accessibility will be irrevocably removed by the applicant upon the granting of the patent.

The identification of the EPY-1 strain with fungal ITS rRNA primer showed sequence homology with *Pichia kluyveri* (Ascomycota; Saccharomycotina; *Saccharomyces*; Saccharomycetales; Saccharomycesceae; *Pichia*), a yeast with broad natural occurrence, which was predominantly isolated from rotting fruits and plants (Phaff, H. J., et al., *Pichia barkeri*, a New Yeast Species Occurring in Necrotic Tissue of *Opuntia stricta*. International Journal of Systematic and Evolutionary Microbiology, 1987. 37 (4): p. 386-390).

In particular, the incorporation of yeast strain according to the present disclosure and/or of a lysate, filtrate, isolate or extract thereof negatively influences the survival of insects like aphids or *Drosophila*.

The term "isolated" describes any molecule separated from its natural source.

As used herein, the term "homologous" or "homologs", with reference to a nucleic acid sequence, includes a nucleotide sequence that hybridizes under stringent conditions to one of the coding sequences of SEQ ID NO: 3. SEQ ID NO. 4, SEQ ID NO. 5. SEQ ID NO. 6 or SEQ ID NO. 7, or the complements thereof. Sequences that hybridize for example under stringent conditions to SEQ ID NO:3, or the complements thereof, are those that allow an antiparallel alignment to take place between the two sequences, and the two sequences are then able, under stringent conditions, to form hydrogen bonds with corresponding bases on the opposite strand to form a duplex molecule that is sufficiently stable under the stringent conditions to be detectable using methods well known in the art. Substantially homologous sequences have preferably from about 70% to about 80% sequence identity, or more preferably from about 80% to about 85% sequence identity, or most preferable from about 90% to about 95% sequence identity, to about 99% sequence identity, to the referent nucleotide sequences of SEQ ID NO: 3, SEQ ID NO. 4. SEQ ID NO. 5, SEQ ID NO. 6 or SEQ ID NO. 7 as set forth in the sequence listing, or the complements thereof.

As used herein, the term "control" or "controlling" as in e.g., the phrase: the "control" of pests or pest populations, or "controlling" pests or pest populations, or as in the phrase: "controlling" pests, refers to preventing, reducing, killing, inhibiting the growth of, or elimination of a pest or population of pests as defined herein. Indeed, "control" or "controlling" as used herein refers to any indicia of success in prevention, killing, inhibition, elimination, reduction or amelioration of a pest or pest population. In particular "pest control" refers to the removal or the reduction of harm of pests. The concept of "pest control" include reducing of the target pest, killing of pests (extermination), pest proliferation inhibition, pest development inhibition, pest growth inhibition, repelling of pests (repellence), reducing of the survival rate of the target pest and the removal or the reduction of harm of pests.

The term "pest" refers to any animal of the scientific classification (phylum) Nematoda (e.g., root-knot nematode, soybean cyst nematode, etc.), Arthropoda including Insecta, (e.g., white flies, thrips, weevils, etc.) and/or Arachnida. (e.g., mites, ticks, spiders, etc.).

Therefore, as used herein, the term "target pest" refers to insects, arachnids, crustaceans, fungi, bacteria, viruses, nematodes, flatworms, roundworms, pinworms, hookworms, tapeworms, trypanosomes, schistosomes, botflies, fleas, ticks, mites, and lice and the like that are pervasive in the human environment and that may ingest or contact one or more cells, tissues, or fluids produced by a pest host or symbiont transformed to express or coated with a double stranded gene suppression agent or that may ingest plant material containing the gene suppression agent.

These include for example, leaf-feeding insects including insects of the order Coleoptera (beetles) such as Chrysomelidae: *Leptinotarsa decemlineata* (Say) (Colorado potato beetle) and *Diabrotica* spp. (corn rootworm), insects of the order Lepidoptera such as *Plutella xyostella* (Linnaeus) (diamondback moth) and sucking insects including insects of the order Coleoptera (beetles) such as Chrysomelidae: *Leptinotarsa decemlineata* (Say) (Colorado potato beetle) and *Diabrotica* spp. (corn rootworm), insects of the order Lepidoptera such as *Plutella xyostella* (Linnaeus) (diamondback moth) and sucking insects of the order Homoptera, in particular of the genus Bemisia such as *Bemisia argentifolii* Bellows & Perring (silverleaf whitefly). Other agriculturally important insects include, for example. Lepidoptera, Noctuidae: *Trichoplusia ni* (cabbage looper), *Pseudoplusia includens* (soy bean looper), *Agrotis ipsilon* (black cutworm), *Caenurgina erechtea* (forage looper), *Helicoverpa zea* (corn earworm), *Heliothis virescens* (tobacco budworm), *Spodoptera frugiperda* (fall armyworm), *Spodoptera exigua* (beet army worm). *Spodoptera ornithogalli* (yellowstriped armyworm), *Anagrapha falcifera* (celery looper), and *Pseudalenia unipuncta* (armyworm). *Anticarsia gemmatalis* (velvetbean caterpillar); Plutellidae: *Plutella xylostella* (diamondback moth); Pyralidae: *Achyra rantalis* (garden webworm), *Desmia funeralis* (grape leaffolder), *Diaphania hyalinata* (melonworm), and *Diaphania nitidalis* (pickleworm); Sphingidae; *Manduca quinquemaculata* (tomato hornworm), *Manduca sexta* (tobacco hornworm), *Eumorpha achemon* (achemon sphinx), *Agrius cingulata* (sweetpotato hornworm), and *Hyles lineata* (whitelined sphinx); moths such as gypsy moth (*Lymantria dispar*).

The present disclosure pertains to pest control methods comprising incorporating a yeast strain belonging to the species *Pichia kluyveri* and/or with a lysate, filtrate, isolate or extract thereof into the body of an agricultural target pest, wherein the target pest is an insect belonging to the order Hemiptera and the uptake by the target pest of said inhibitor reduce at least the reproduction and/or survival (or survival rate) of said target pest. In particular, the yeast strain belonging to the species *Pichia kluyveri* AT can be identified with the ITS primers SEQ ID NO: 1 and SEQ ID NO:2, or homologs thereof, wherein said homologs may have a sequence identity of at least 80%, in particular of at least 85%, in particular of at least 90%, in particular of at least 95%, 96%, 97%, 98%, 99% to SEQ ID NO: 1 and/or SEQ ID NO:2.

In an advantageous example, said yeast strain belonging to the species *Pichia kluyveri* comprises an ITS sequence selected from the group consisting of SEQ ID NO:3. SEQ ID NO:4, SEQ ID NO:5, SEQ ID NO:6 and SEQ ID NO: 7 or homologs thereof, wherein said homologs may have a sequence identity of at least 80%, in particular of at least 85%, in particular of at least 90%, in particular of at least 95, 96%, 97%, 98%, 99% to SEQ ID NO:3, SEQ ID NO:4, SEQ ID NO:5, SEQ ID NO:6 or SEQ ID NO:7.

In advantageous embodiments of the present disclosure, the target pests are insects belonging to the insect order Hemiptera also known as the true bugs. Many Hemipteran insects are important agricultural pests because they cause direct feeding damage to their host plants and/or transmit plant disease agents including viruses and bacteria. Microscopic and behavioral studies on different Hemiptera species showed that their exuviae (molted skins) normally had either fully or partially extended stylets in a feeding-like position. In most cases these stylets were still partially embedded in their host plants after ecdysis, which indicated that plant-feeding hemipteran nymphs use their stylets to anchor themselves to host plants during molting.

Advantageous examples of the target pests belonging to Hemiptera include insects of the suborder Sternorrhyncha including aphids. In particular, examples of the target pests belonging to Hemiptera include *Nilaparvata lugens, Sogatella furcifera, Laodelphax stratella, Nephotettix cincticeps, Recilia dorsalis, Stenotus rubrovittatus, Trigonotylus caelestialium, Leptocorisa chinensis, Nezara antennata, Nezara viridula, Lagynotomus elongatus, Scotinophara lurida, Eysarcoris annamita, Evsarcoris lewisi, Eysarcoris ventralis, Togo hemipterus* Scott, *Cletus punctiger, Piezodorus hybneri, Halyomorpha halys, Dolycoris baccarum, Neotoxoptera formosana, Rhopalosiphum padi, Rhopalosiphum maidis, Acyrthosiphon pisum* and *Aphis glycines*.

In advantageous embodiments, the target pests are belonging to the genera of aphids, in particular *Acyrthosiphon pisum*.

Further advantageous examples the target pest is an insect belonging to the family Drosophilidae, in particular wherein the target pest belonging to the genus *Drosophila*, in particular wherein the target pest belonging to the species of *Drosophila suzukii* and/or *Drosophila melanogaster*.

In advantageous embodiments, the target pests are belonging to flies of the Drosophilidae family, particularly *Drosophila suzukii*, which is herein also referred to as "*D. suzukii*" or "spotted-wing *drosophila*" (SWD) and/or the target pest is *Drosophila melanogaster*.

As used herein, "derived from" means directly isolated or obtained from a particular source or alternatively having identifying characteristics of a substance or organism isolated or obtained from a particular source. In the event that the "source" is an organism, "derived from" means that it may be isolated or obtained from the organism itself or medium used to culture or grow said organism.

As used herein, "whole broth culture" refers to a liquid culture containing both cells and growth media. If yeast are grown on a plate the cells can be harvested in water or other liquid, whole culture.

As used herein, the term "supernatant" refers to the liquid that lies above the cell sediment or precipitate. The "supernatant" is the remaining liquid when cells grown in broth or cells harvested in another liquid from an agar plate, are removed by centrifugation, filtration, sedimentation, or other means well known in the art.

As defined herein, "filtrate" refers to liquid from a whole broth culture that has passed through a filter, and which had been separated from the filtrate.

As defined herein, "isolate" refers to substantially cell free isolate derived from yeast cells like a yeast protein isolate.

As defined herein, "extract" refers to a substance separated from cells by liquid-liquid extraction, solid phase extraction, acid-base extraction, mechanochemical-assisted extraction, ultrasound-assisted extraction or other method. For the common liquid-liquid extraction, a solvent (water, detergent, buffer) is used to separate the "extract" from the. Yeast extract according to the present disclosure includes a complex and widely used hydrolysate of yeasts.

As used herein, the term "insecticide" or "insecticidal" is intended to refer to any agent or combination of agents capable of killing one or more insects and/or inhibiting the growth of one or more insects. As used herein, the term "acaricide" or "acaricidal" is intended to refer to any agent or combination of agents capable of killing one or more acarids and/or inhibiting the growth of one or more acarids.

As used herein, the term "carrier" is intended to refer to an "agronomically acceptable carrier." An "agronomically acceptable carrier" is intended to refer to any material which can be used to deliver the actives (e.g. a yeast strain belonging to the species *Pichia kluyveri* and/or a lysate, filtrate, isolate or extract thereof) to a plant or plant part (e.g., foliage or seed). As used herein, the term "soil-compatible carrier" is intended to refer to any material that can be added to a soil without causing/having an adverse effect on plant growth, soil structure, soil drainage, or the like.

In yet an even more particular embodiment, the yeast strain is a yeast strain belonging to the species *Pichia kluyveri*, in particular the strain *Pichia kluyveri* EPY-1 that was deposited on Jan. 17, 2020 under the accession number DSM 33403 according to the requirements of the Budapest Treaty at the Deutsche Sammlung von Mikroorganismen und Zellkulturen (DSMZ). Inhoffenstraße 7B, 38124 Braunschweig (DE) by Fraunhofer Institute for Molecular Biology and Applied Economy IME, Winchesterstr.2, 35394 Giessen. Germany. Cultures of the deposited yeast strain may consist of viable yeasts, including whole broth cultures. In another embodiment, the deposited strain(s) is a biologically pure culture (e.g, cultures having a purity of at least 60%, of at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, up to 100% pure). In another embodiment, the strain is a variant of *Pichia kluyveri* EPY-1. As used herein, the term variant shall mean a yeast which is (i) a progeny (unmodified descendants) of the strain of *Pichia kluyveri* EPY-1 and (ii) modified descendants of *Pichia kluyveri* EPY-1.

The identification of the *Pichia kluyveri* EPY-1 with fungal ITS rRNA primer (e.g. SEQ ID NO.1 and SEQ ID NO. 2) showed sequence homology with *Pichia kluyveri* (Ascomycota; Saccharomycotina; *Saccharomyces*; Saccharomycesles; Saccharomycesceae; *Pichia*), a yeast with broad natural occurrence, which was predominantly isolated from rotting fruits and plants.

In particular for the pest control method according to the present disclosure, the yeast strain belonging to the species *Pichia kluyveri* can be identified with the ITS primers SEQ ID NO: 1 and SEQ ID NO:2, or homologs thereof. In some advantageous embodiments, the yeast strain belonging to the species *Pichia kluyveri* comprises an ITS sequence selected from the group consisting of SEQ ID NO:3, SEQ ID NO:4, SEQ ID NO:5, SEQ ID NO:6 and SEQ ID NO:7 or homologs thereof, wherein said homologs may have a sequence identity of at least 80%, in particular of at least 85%, in particular of at least 90%, in particular of at least 95%, 96%, 97%, 98%, 99% to SEQ ID NO:3, SEQ ID NO:4, SEQ ID NO:5. SEQ ID NO:6 or SEQ ID NO:7 and having the properties of the isolated *Pichia kluyveri* EPY-1 strain, in particular the property of reducing the survival of a target pest, in particular of a target pest belonging to the family of aphids like *Acyrthosiphon pisum* and/or a target pest belonging to the species of *Drosophila suzukii* and/or *Drosophila melanogaster*.

The *Pichia kluyveri* strains described herein, and in particular, the strain having deposit accession number DSM 33403 and variants thereof, are cultivated in nutrient medium using methods known in the art. Suitable media are available may be available from commercial sources or prepared according to published compositions. Non-limiting examples of acceptable growth media include lysogeny broth (LB) medium, 2×YT medium, yeast extract-peptone-dextrose (YPD) medium, De Man, Rogosa and Sharpe (MRS) medium, etc. and their agar plate derivates. In some advantageous embodiments, the used *Pichia kluyveri* strains in the methods of the present disclosure are not *Pichia guilliermondii* strains.

The yeasts may be cultivated by shake flask cultivation, small scale or large-scale fermentation (including but not limited to continuous, batch, fed-batch, or solid-state fermentations) in laboratory or industrial fermenters performed in suitable medium and under conditions allowing cell growth. The cultivation may take place in suitable nutrient medium comprising carbon and nitrogen sources and inorganic salts, using procedures known in the art. These culture methods may be used in the preparation of an inoculum of *Pichia kluyveri* for coating seeds and/or application to carrier to be applied to plants, plant parts, or soil.

The present disclosure is also directed to extracts obtained from the strain that have insecticidal activity Extraction of toxin from the cells is accomplished using procedures known in the art. Exemplary procedures include: adding 0.1% detergent or 0.1% CHAPS buffer to a cell pellet in equal volume of the original culture: extraction is for 30 minutes with shaking at room temperature. Cells are removed by centrifugation: the supernatant contains the toxin. The entire extract without removal of the cells is also toxic.

The present disclosure is further directed to methods of controlling insects using *Pichia kluyveri*. This aspect includes application of an effective insect control amount of the strain, application of an effective insect control amount of a supernatant, filtrate, lysate or extract containing an insecticidally active metabolite produced by the strain or application of combinations of the foregoing. The strain, supernatant, filtrate, or extract is applied, alone or in combination, in an effective insect control or insecticidal amount. For the purposes of this invention, an effective amount is defined as that quantity of *Pichia kluyveri* cells, supernatant, filtrate, isolate, lysate or extract, alone or in combination that is sufficient to kill the target insect, increase mortality, or inhibit the incidence, growth, development or reproduction of the target insect. Typically, a concentration range about $4 \times 10^7$ to $2 \times 10^{10}$ colony forming units (CFU)/ml is effective. The effective rate can be affected by insect species present, stage of insect growth, insect population density, and environmental factors such as temperature, wind velocity, rain, time of day and seasonality. The amount that will be within an effective range in a particular instance can be determined by laboratory or field tests.

The strain and/or supernatants, lysates, isolates, filtrates or extracts encompassed herein are useful for controlling insects (organisms in the class Insecta), and find particular use for control of a variety of agronomical important insects. The strain and/or insecticidal active metabolites obtained from the strain are useful for control of insect pests.

The invention also encompasses compositions, which incorporate the strain of the invention, and/or compositions comprising an insecticidal-active metabolite produced by the strain of the invention and/or supernatants, lysates, isolates, filtrates or extracts of *Pichia Kluyveri*. Such compositions include, for example, whole broth cultures, liquid cultures, or suspensions of the strain: supernatants, filtrates, lysates, isolates or extracts obtained from the strain or combinations of the foregoing. Such insecticidal-active compositions may optionally include other ingredients such as an agricultural carrier, insect feeding stimulant, insect pheromone, insect attractant, fungicide, insecticide, photoactive dye, fluorescent brighteners, spreading agent, sticking agent, thickener, emulsifier, stabilizer, preservative, buffer, water, diluent or other additive as known in the art of formulation of insecticidal compositions. Insect feeding stimulants include, for example, cucurbitacins, e.g., cucurbitacin E-glycoside as described by Schroder et al. in U.S. Pat. Nos. 5,968,541 and 6,090,398. Photoactive dyes in combination with biological control agents are described by Martin et al., 1998. Fluorescent brighteners include, for example, those which provide protection for pathogens from the damaging effects of exposure to UV radiation and which may enhance biological activity of an organism as described by Shapiro et al. in U.S. Pat. No. 5,124,149. The yeast biocontrol composition of the invention may also contain other insect biocontrol strains. The compositions are applied as known in the art to protect plants from insect pests. The compositions are applied in an area where a target insect is to be controlled, for example, application to soil in a field or surrounding a plant, to a target plant, e.g., to plant roots, on plant foliage, flowers, stems, seed, and tubers. The strain of the invention can be grown on rice grains and the rice grains applied to the plant or soil. Application of the compositions of the invention are carried out by any means known in the art, for example, spreading, spraying, drenching, drip irrigation of the insecticidal composition.

The manner for the incorporation of a composition comprising a *Pichia kluyveri* strain and/or of a lysate, filtrate, isolate or extract thereof is not particularly limited and may be selected according to the target pest. When the target pest is a pest that attacks a plant, for example, the agent (pesticide) containing the composition is in advance retained in the plant, which is to be attacked by the target pest, through application, spraying, or atomization. Because of this, when the target pest ingests the plant, the composition is incorporated into the body of the target pest. The incorporation of the composition may be done by topical application, uptake through respiratory system etc.

The term "incorporating" includes any method by which a pest may uptake or come in contact with a composition comprising a *Pichia kluyveri* strain and/or of a lysate, filtrate, isolate or extract thereof. A pest may be exposed to the composition by direct uptake (e.g. by feeding). Alternatively, a pest may come into direct contact with a composition comprising a *Pichia kluyveri* strain and/or of a lysate, filtrate, isolate or extract thereof. For example, a pest may come into contact with a surface or material treated with a composition comprising a *Pichia kluyveri* strain and/or of a lysate, filtrate, isolate or extract thereof. In particular, the target pest may be contacted with the *Pichia kluyveri* strain and/or of a lysate, filtrate, isolate or extract thereof by topical application, uptake through respiratory system etc.

In particular, the *Pichia kluyveri* strain and/or of a lysate, filtrate, isolate or extract thereof may be a coating or a powder that can be applied to a substrate as a means for protecting the substrate from infestation by an insect and thereby preventing pest-induced damage to the substrate or material. Thus, in one embodiment, the composition is in the form of a coating on a suitable surface that adheres to and is eventually ingested by an insect which comes into contact with the coating. Such a composition can be used to protect any substrate or material that is susceptible to infestation by or damage caused by a pest, for example, foodstuffs and other perishable materials, and substrates such as wood.

For example, the *Pichia kluyveri* strain and/or of a lysate, filtrate, isolate or extract thereof may be comprised in a liquid that is brushed or sprayed on the target pest. In particular, the *Pichia kluyveri* strain and/or of a lysate, filtrate, isolate or extract thereof is incorporated by delivering via ingestion, application, spraying and/or atomization on the target pest.

On the other hand, when a feed (feed agent) containing the *Pichia kluyveri* strain and/or of a lysate, filtrate, isolate or extract thereof is placed at the site of occurrence or in the route of entry of the target pest, the target pest ingests the feed, and thus the *Pichia kluyveri* strain and/or of a lysate, filtrate, isolate or extract thereof is incorporated into the body of the target pest.

EXAMPLES

In the following examples, materials and methods of the present disclosure are provided including the determination of the effect of *P. kluyveri* on survival of the target pests. It should be understood that these examples are for illustrative purpose only and are not to be construed as limiting this disclosure in any manner. All publications, patents, and patent applications cited herein are hereby incorporated by reference in their entirety for all purposes.

Example 1

Oral Feeding Protocol with *D. suzukii* and *D. melanogaster*

*P. kluyveri* cultures were grown overnight at 37° C. and shaken at 220 rpm. The overnight culture was centrifuged at 2000 g and the pellet was resuspended in 2 mL 50 mM sucrose to an $OD_{600}$ of 1.

50 mM sucrose is used as a negative control. The suspension was transferred to 2.5 cm Ø vials with three layers of paper towel. Twenty female flies were transferred to the vials and allowed to feed on the yeast, with temperature and humidity maintained at 26° C. and 60%. The number of surviving flies was counted daily and 200 µL of 100 mM sucrose was added to the vials to maintain humidity and replace nutrients. The experiments were conducted at least three times independently.

Figure 2:
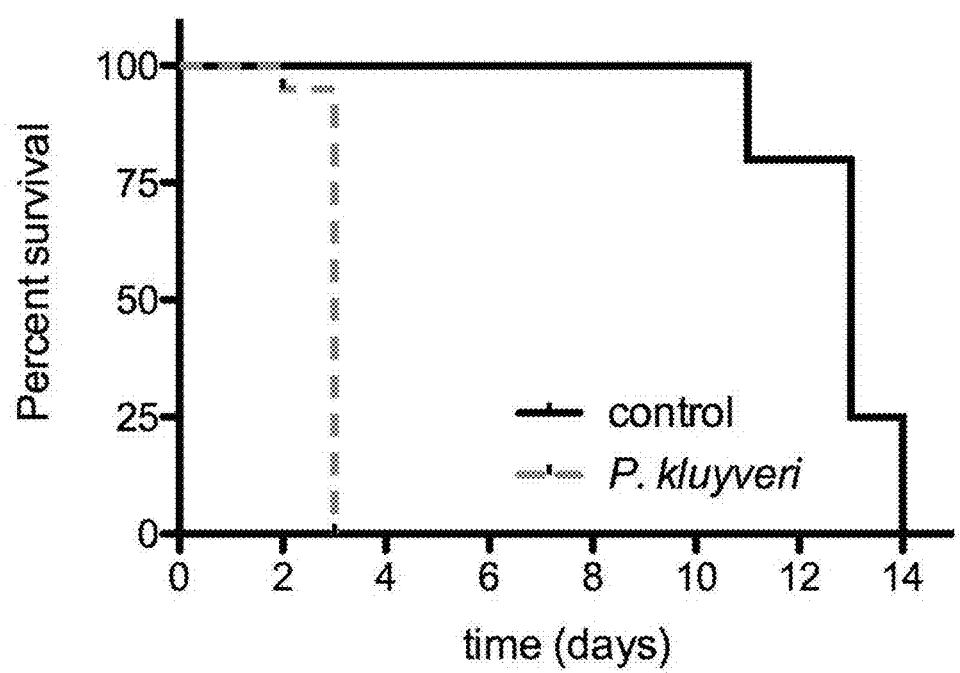
FIG. 2 is a diagram showing survival data of *Drosophila suzukii* after feeding with *Pichia kluyveri* EPY-1.

FIG. 2 is a diagram showing that the yeast strain *Pichia kluyveri* EPY-1 has insecticidal activity, if it is orally fed to *Drosophila suzukii*.

Figure 8:
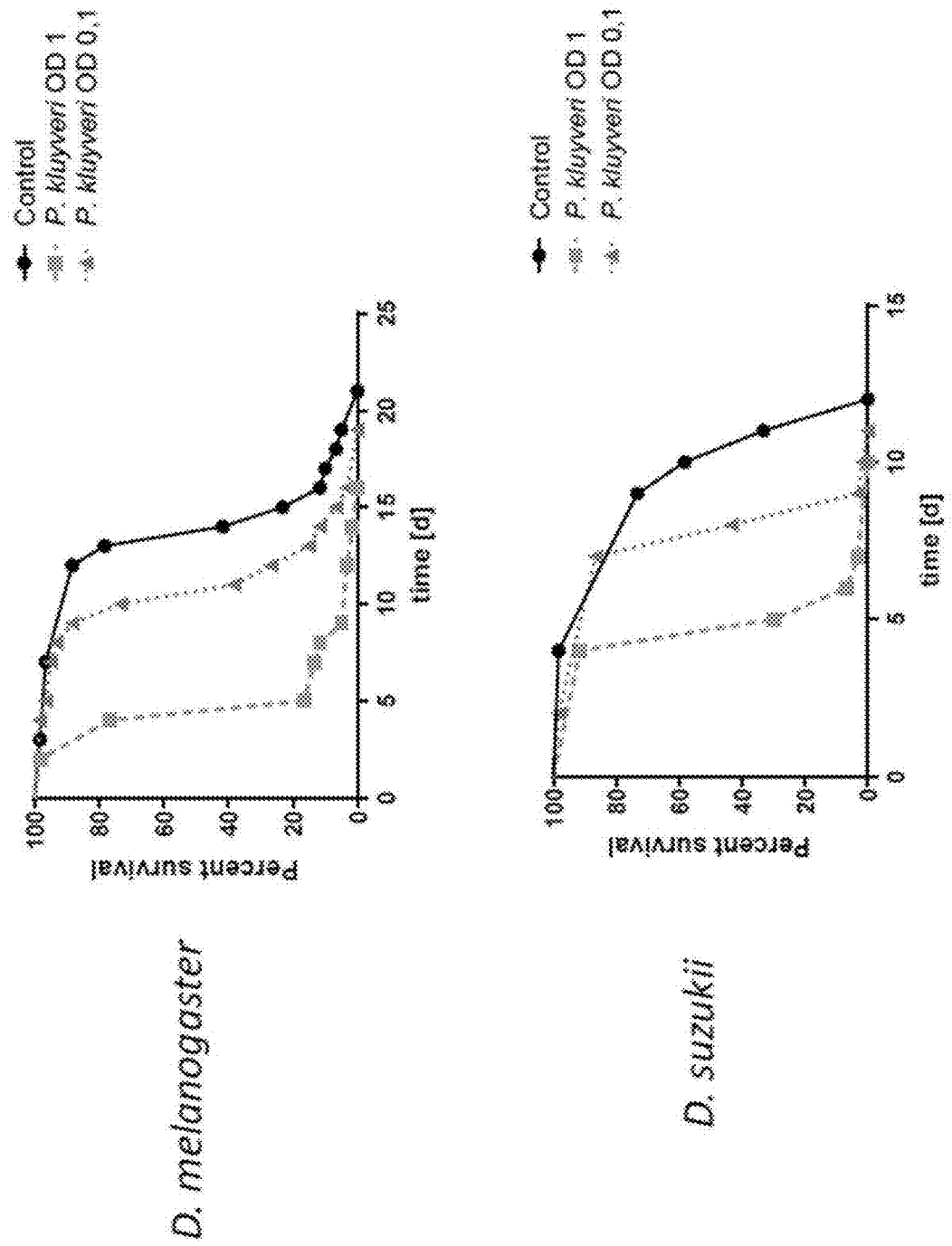
FIG. 8 depicts diagrams showing that the oral infection with viable *Pichia kluyveri* EPY-1 leads to a significant effect on survival of *D. melanogaster* and *D. suzukii*.

FIG. 8 depicts diagrams showing that the oral infection with viable *Pichia kluyveri* EPY-1 leads to an significant effect on survival of *D. melanogaster* and *D. suzukii*.

Example 2

Oral Feeding with *Acyrthosiphon pisum* (Pea Aphid)

The pea aphid *A. pisum* was orally fed with 30 µL of *P. kluyveri* solution with an $OD_{600}$ of 0.1 and 1. The yeast suspension were transferred on the base of 24-well-plates and covered with parafilm. Survival experiments were performed three times independently. Oral feeding of *A. pisum* with *P. kluyveri* with $OD_{600}$ of 0.1 and 1 showed effects and significant results just with the lower concentration used.

Figure 3:
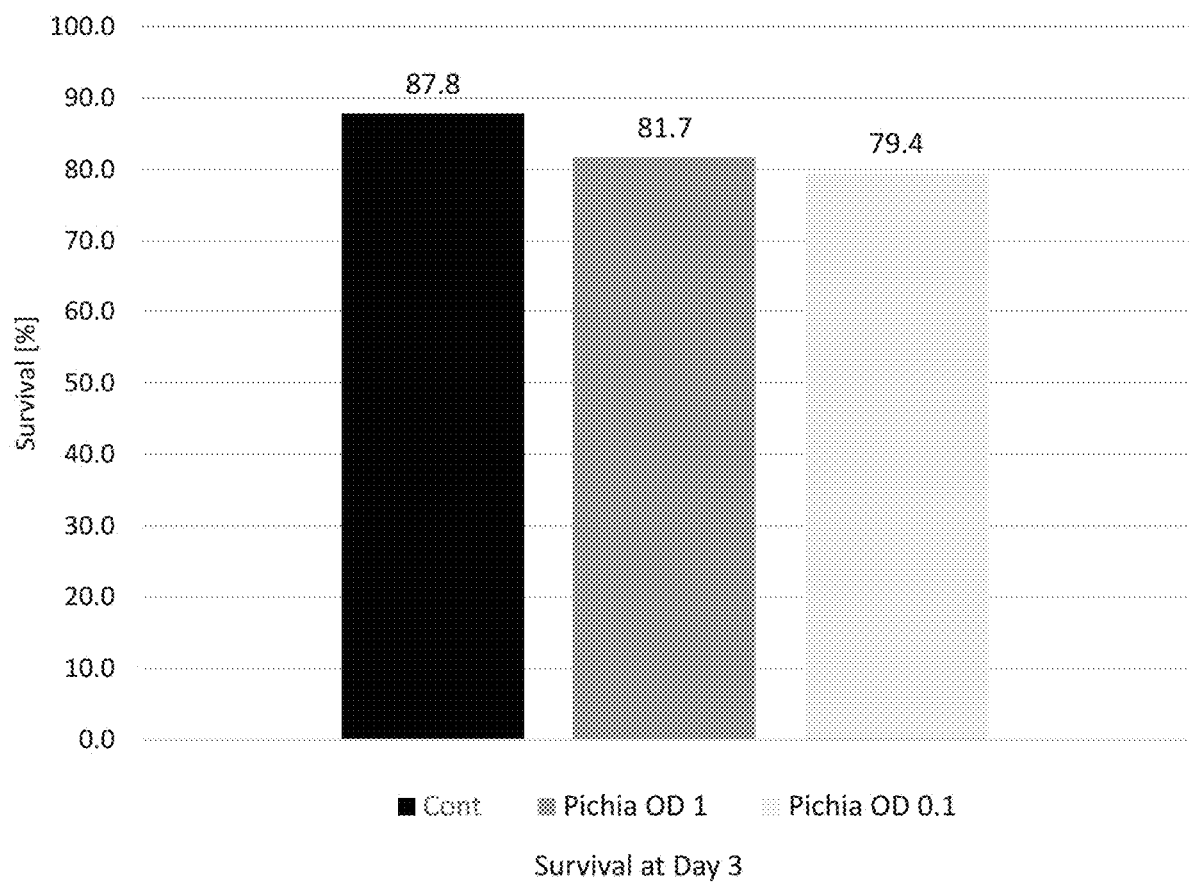
FIG. 3 is a diagram showing survival data of *A. pisum* after feeding with *Pichia kluyveri* EPY-1.

FIG. 3 is a diagram showing that the yeast strain *Pichia kluyveri* EPY-1 has insecticidal activity, if it is orally fed to *A. pisum*.

Example 3

Injections with *Acyrthosiphon pisum* (Pea Aphid)

Figure 4:
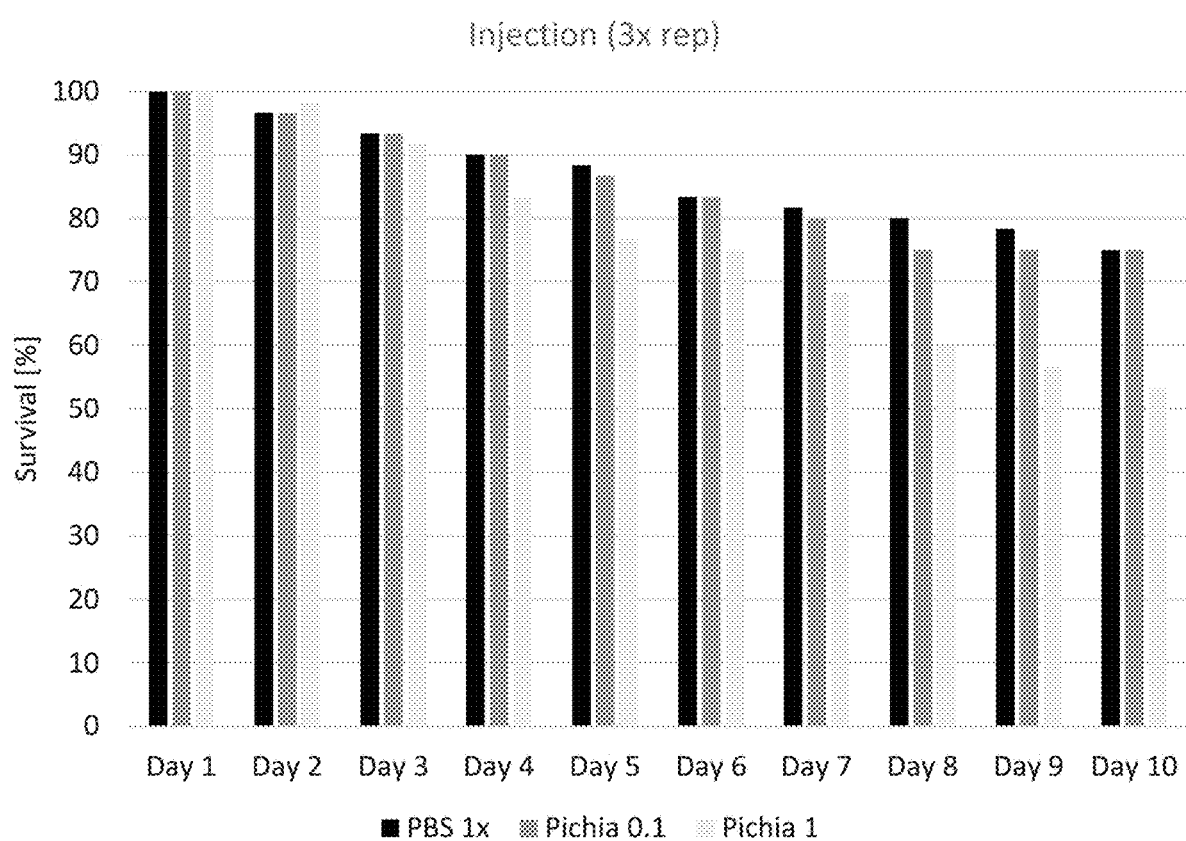
FIG. 4 is a diagram showing survival data of *A. pisum* after injection with *Pichia kluyveri* EPY-1.

25 nL of *P. kluyveri* of an $OD_{600}$ of 0.1 and 1 were injected into *A. pisum*. Aphids were fixed with vacuum and were injected between the middle and hindlegs. For the injections a M3301 micromanipulator (World Precisions Instruments, Hitchin, UK) with glass capillaries were used. Phosphate-buffered-saline (PBS) was used as negative injection control. Injection of live yeast had an impact on the survival of the tested aphids. Survival data of *A. pisum* after injection of *P. kluyveri*. Significant decrease detectable for infection with *P. kluyveri* using an $OD_{600}$ of 1 (FIG. 4).

REFERENCES

All publications, patents, and patent applications cited in the present application are hereby incorporated by reference in their entirety for all purposes.

1 Beckmann, M. and Haack, K. J.: Insektizide für die Landwirtschaft: Chemische Schädlingsbekämpfung, in: Chemie in unserer Zeit 2003, 37, 88-97; doi: 10.1002/ciuz.200300268.
2. Hallmann, C. A., et al., More than 75 percent decline over 27 years in total flying insect biomass in protected areas. PLOS One, 2017. 12 (10): p. e0185809.
3. Tsvetkov N., Samson-Robert O., Sood K., Patel H. S., Malena D. A., Gajiwala P. H., Maciukiewicz P., Fournier V., Zayed A. Science. 2017 Jun. 30; 356 (6345): 1395-1397. doi: 10.1126/science.aam7470.
4. Whitehorn P. R., O'Connor S., Wackers F. L., Goulson D. Science. 2012 Apr. 20; 336 (6079): 351-2. doi: 10.1126/science. 1215025. Epub 2012 Mar. 29.
5. Rundlöf M., Andersson G. K., Bommarco R., Fries I., Hederström V., Herbertsson L., Jonsson O., Klatt B. K., Pedersen T. R., Yourstone J., Smith H. G. Nature. 2015 May 7; 521 (7550): 77-80. doi: 10.1038/nature14420. Epub 2015 Apr. 22.
6. Cassereau J., Ferré M., Chevrollier A, Codron P, Vemy C, Homedan C, Lenaers G, Procaccio V, May-Panloup P, Reynier P. Curr Med Chem. 2017; 24 (27): 2988-3001. doi: 10.2174/0929867324666170526122654.
7. Phaff, H. J., et al., *Pichia barkeri*, a New Yeast Species Occurring in Necrotic Tissue of *Opuntia stricta*. International Journal of Systematic and Evolutionary Microbiology, 1987. 37 (4): p. 386-390.
8. Masoud, W. and L. Jespersen, Pectin degrading enzymes in yeasts involved in fermentation of *Coffea arabica* in East Africa. International Journal of Food Microbiology, 2006. 110 (3): p. 291-296.
9. Björnberg, A. and Schnürer, J., Canadian Journal of Microbiology. 1993. 653 (39): 623-628.

What is claimed is:

1. A pest control method for reducing the survival of a target pest, the method comprising contacting by a means suited for uptake by the target pest, a yeast strain belonging to the species *Pichia kluyveri* and/or with a lysate, filtrate, isolate or extract thereof, wherein the target pest belongs to the species *Drosophila suzukii* and/or *Drosophila melanogaster* and wherein the yeast strain belonging to the species *Pichia kluyveri* is identifiable with ITS primers of SEQ ID NO:1 and SEQ ID NO:2, or homologs thereof having a sequence at least 85% identical to SEQ ID NO: 1 and/or SEQ ID NO:2.

2. The pest control method according to claim 1, wherein the yeast strain belonging to the species *Pichia kluyveri* and/or a lysate, filtrate, isolate or extract thereof is comprised in a composition in combination with a carrier.

3. The pest control method according to claim 1, wherein the yeast strain belonging to the species *Pichia kluyveri* and/or a lysate, filtrate, isolate or extract thereof is orally fed to the target pest and/or sprayed on a crop or part of a crop for contacting the target pest.

4. The pest control method according to claim 1, further comprising spraying, or atomization of a crop in advance of the contact for incorporating the composition into the body of the target pest by ingestion of the crop or a part thereof.

5. The pest control method according to claim 1, which reduces the survival of the target pest, wherein the yeast strain belonging to the species *Pichia kluyveri* is selected from the group consisting of *Pichia kluyveri* EPY-1 (DSMZ Accession number 33403), yeast strains derived therefrom, and progenies or mutants thereof, wherein the mutants retain the properties of *Pichia kluyveri* EPY-1.

6. The pest control method according to claim 1, wherein lysate, filtrate, isolate or extract reduces survival rate of the target pest.

7. The pest control method according to claim 1, wherein the yeast strain is identifiable by the ITS primers of SEQ ID NO:1 and SEQ ID NO:2.

8. The pest control method according to claim 1, wherein the yeast strain identifiable by the homologs of the ITS primers of SEQ ID NO:1 and SEQ ID NO:2 reduces survival rate of the target pest.

* * * * *